US007689441B1

(12) United States Patent
Craft

(10) Patent No.: US 7,689,441 B1
(45) Date of Patent: Mar. 30, 2010

(54) INTEGRATED ORDER AND SCHEDULING IN A HEALTHCARE ADMINISTRATION SYSTEM

(75) Inventor: Richard Craft, Medford, NJ (US)

(73) Assignee: Siemens Medical Solutions Health Services Corporation, Malvern, PA (US)

(*) Notice: Subject to any disclaimer, the term of this patent is extended or adjusted under 35 U.S.C. 154(b) by 2598 days.

(21) Appl. No.: 10/197,925

(22) Filed: Jul. 18, 2002

Related U.S. Application Data

(60) Provisional application No. 60/313,646, filed on Aug. 20, 2001.

(51) Int. Cl.
G06F 19/00 (2006.01)

(52) U.S. Cl. .................... 705/3; 705/2; 705/8; 600/300

(58) Field of Classification Search ............... 705/2, 705/3, 8; 600/300
See application file for complete search history.

(56) References Cited

U.S. PATENT DOCUMENTS

| | | | | |
|---|---|---|---|---|
| 5,065,315 A * | 11/1991 | Garcia | ............................ | 705/2 |
| 5,113,380 A | 5/1992 | Levine | ........................ | 368/10 |
| 5,558,638 A | 9/1996 | Evers et al. | ................... | 604/66 |
| 5,737,728 A | 4/1998 | Sisley et al. | ..................... | 705/8 |
| 5,748,907 A * | 5/1998 | Crane | ........................... | 705/2 |
| 5,764,923 A | 6/1998 | Tallman et al. | ................. | 705/3 |
| 5,772,585 A | 6/1998 | Lavin et al. | .................. | 600/300 |
| 5,815,566 A | 9/1998 | Ramot et al. | ........... | 379/210.01 |
| 5,970,466 A | 10/1999 | Detjen et al. | .................... | 705/8 |
| 5,982,863 A | 11/1999 | Smiley et al. | ............ | 379/88.18 |
| 6,024,699 A | 2/2000 | Surwit et al. | ................ | 600/300 |
| 6,047,259 A | 4/2000 | Campbell et al. | .............. | 705/3 |
| 6,061,657 A | 5/2000 | Whiting-O'Keefe | ........... | 705/2 |
| 6,151,581 A | 11/2000 | Kraftson et al. | ................ | 705/3 |
| 6,208,974 B1 | 3/2001 | Campbell et al. | .............. | 705/3 |
| 6,308,160 B1 | 10/2001 | Rex | ............................... | 705/6 |
| 6,345,260 B1 * | 2/2002 | Cummings et al. | ............. | 705/8 |
| 6,349,238 B1 | 2/2002 | Gabbita et al. | .............. | 700/101 |
| 6,351,770 B1 | 2/2002 | Li et al. | ....................... | 709/225 |
| 2002/0059082 A1 * | 5/2002 | Moczygemba | ................. | 705/3 |
| 2002/0120472 A1 * | 8/2002 | Dvorak et al. | .................. | 705/3 |
| 2002/0194029 A1 * | 12/2002 | Guan et al. | .................... | 705/3 |
| 2003/0208391 A1 * | 11/2003 | Dvorak et al. | .................. | 705/8 |
| 2004/0039626 A1 * | 2/2004 | Voorhees | ....................... | 705/9 |

* cited by examiner

Primary Examiner—Gerald J. O'Connor
Assistant Examiner—Lena Najarian
(74) Attorney, Agent, or Firm—Alexander J Burke

(57) ABSTRACT

A healthcare administration system integrates the entry of an order for a medical service for a patient with the scheduling of an appointment for performing the service. The system incorporates receiving service order information for a medical service for a patient from a user; generating an order for the medical service based upon the service order information; and enabling the user to perform one or more tasks selected from the group consisting of (a) scheduling an appointment with a provider of the medical service, (b) storing the order information in a queued waitlist, and (c) automatically rescheduling the appointment based upon the queued waitlist.

32 Claims, 8 Drawing Sheets ically available in healthcare administration systems for placement of orders for patient services do not support an easy, efficient mechanism for authorized users to also schedule an appointment for service delivery from within the order placing workflow. This results in fragmentation of the service delivery process for schedulable services, requiring the user to enter a separate scheduling workflow to obtain an appointment for service delivery.
INTEGRATED ORDER AND SCHEDULING IN A HEALTHCARE ADMINISTRATION SYSTEM This is a non-provisional application of provisional application Ser. No. 60/313,646 by R. Craft et al. filed Aug. 20, 2001.

BACKGROUND OF THE INVENTION

1. Field of the Invention

This invention is related to a heathcare administration system having an integrated order and scheduling system. Particularly, the invention is directed to an integrated order and scheduling system that allows an order to be scheduled quickly and efficiently from within the order placing workflow. In addition, the invention allows appointments to be placed on a waitlist and rescheduled directly therefrom.

2. Description of the Prior Art

Order processing products currently available in healthcare administration systems for placement of orders for patient services do not support an easy, efficient mechanism for authorized users to also schedule an appointment for service delivery from within the order placing workflow. This results in fragmentation of the service delivery process for schedulable services, requiring the user to enter a separate scheduling workflow to obtain an appointment for service delivery.

In the best-case scenario, the user performs several additional, redundant steps to obtain an appointment for service delivery. The most common scenario is that the process is split between two users: one who enters orders and another who schedules appointments. Typically, this 'division of labor' results in significant delays to the appointment making process. Consequently, available appointment times are pushed further into the future, delaying patient care.

Existing products on the market also do not provide integrated support for placing appointments on a waitlist, so that appointments can potentially be re-scheduled at an earlier time, for example in the event of a cancellation. In commercially available systems, appointments are typically manually placed on a waitlist for later scheduling. However, manual attempts to manage waitlists for scarce resources are usually ineffective and inconsistently implemented, resulting in failure to equitably address patients' requests. In the absence of an automated, integrated system for placing an order and scheduling or waitlisting an appointment, most scheduling operations are unable to accommodate a patient's request for more desirable appointment times. Consequently, appointment cancellations are more likely to result in failure to re-book the time slot on short notice, reducing resource utilization rates.

It is desirable when placing and scheduling an order for a patient service to ensure that scarce resources are managed in a fair and equitable manner. Efficiently accommodating a patient's request for a more preferable appointment time will increase patient satisfaction by enhancing patient convenience. At the same time, efficiently re-booking a cancelled appointment improves resource productivity through increased resource utilization.

Accordingly, a healthcare administration system is needed that streamlines the order process and the appointment scheduling process, transforming a fragmented workflow into a single, continuous workflow, so that a user who enters a schedulable order may easily and efficiently make an appointment for delivery of that service. A system is further needed that enables the scheduler to place an entry on a waitlist as an integral part of the appointment searching and appointment booking process, so that existing entries on the waitlist may be easily converted to booked appointments through a simple, direct process and waitlist entries may be surveyed as part of the appointment cancellation workflow to expedite processing of the entries.

SUMMARY OF THE INVENTION

The present invention is directed to a healthcare administration system, which integrates the entry of an order for a medical service for a patient with the scheduling of an appointment for performing the service. The system of the present invention incorporates receiving a message signaling generation of an order for a patient to receive the medical service from a user interface; providing appointment availability information from a data source to the user interface in an appointment finder display image; and enabling a user to use the user interface to schedule an appointment with a provider of the medical service for the patient to receive the medical service in response to the received message.

The present invention also incorporates an apparatus for accomplishing the above having a user interface for submitting the service order information; and an interface processor programmed to generate an order for the medical service based upon the service order information; to enable a user to perform one or more tasks selected from the group consisting of (a) scheduling an appointment with a provider of the medical service, (b) storing the order information in a queued waitlist, and (c) automatically rescheduling the appointment based upon the queued waitlist using the user interface, and to enable a user to store (a) the service order information, (b) the order, (c) the scheduled appointment, (d) the queued waitlist, (e) the rescheduled appointment.

DETAILED DESCRIPTION

The present invention will be understood more fully from the detailed description given below and from the accompanying drawings of preferred embodiments of the invention;

which, however, should not be taken to limit the invention to a specific embodiment but are for explanation and understanding only.

Figure 1:
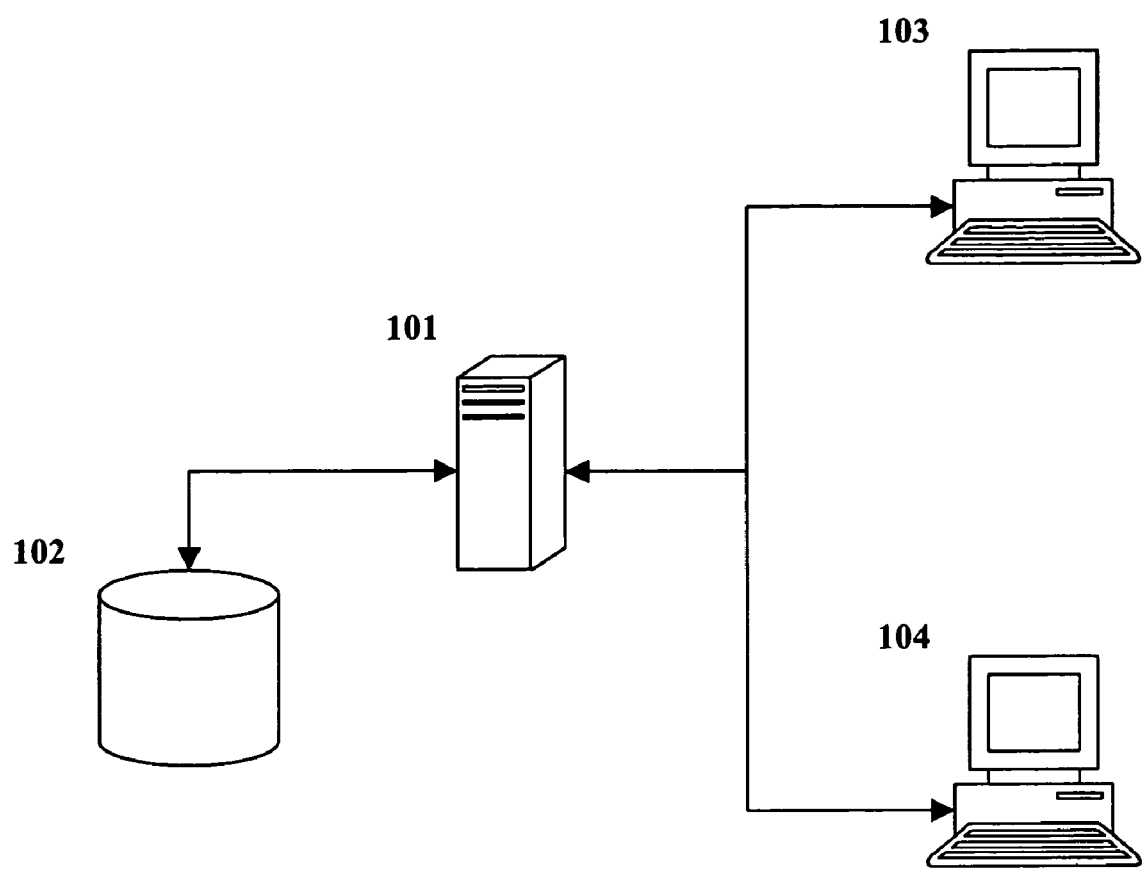
FIG. 1 is a diagram of a preferred embodiment of a computerized healthcare administration system in accordance with aspects of the invention.

The healthcare information system used in the system of an embodiment of the present invention is preferably embodied in a computer software application or applications operating from one or more computer application servers. An exemplary computer system used in connection with the present invention is shown in FIG. 1. As shown in FIG. 1, computer application server 101 contains programming code for implementing the present embodiment. The form of the programming code is not particularly limited and may comprise any software system known in the art capable of performing the aspects of this embodiment.

Information to be used by the software application of computer application server 101 is preferably stored in data storage system 102. Data source or storage 102 may physically form part of computer application server 101, such as through the use of one or more internal storage drives, or data storage 102 may be located separately therefrom. Data may be stored in data source 102 through the use of data interface software code incorporated into the application operating on computer application server 101, or may comprise a separate database application, such as Oracle, Microsoft SQL Server, Sybase, and the like.

Users of the order entry and sample collection system of the present embodiment may enter data directly into computer application server 101 through a user interface displayed thereon, or may access computer application server 101 remotely over a computer network from a user interface displayed on remote computer workstations 103, 104 in a conventional manner. The operation of such systems is well known in the art.

The terms "computer", "computer system", or "server" as used herein should be broadly construed to include any device capable of receiving, transmitting and/or using information including, without limitation, a processor, microprocessor or similar device, a personal computer, such as a laptop, palm PC, desktop, workstation, or word processor, a network server, a mainframe, an electronic wired or wireless device, such as for example, a telephone, an interactive television, such as for example, a television adapted to be connected the Internet or an electronic device adapted for use with a television, a cellular telephone, a personal digital assistant, an electronic pager, a digital watch and the like. Further, a computer, computer system, or system of this embodiment may operate in communication with other systems over a communication network, such as, for example, the Internet, an intranet, or an extranet, or may operate as a stand-alone system, virtual private network, and any other internetworked system.

This embodiment is preferably incorporated as part of a healthcare information system. The healthcare information system is preferably workflow-engineered to synchronize processes across the health enterprise, incorporates a smart user interface that anticipates the needs and unique processes of individual users; and is designed with embedded analytics that empower users to monitor, measure and act. The system architecture is preferably object-oriented and may be run in-house or hosted in a remote Information Services Center. While the preferred embodiment of the system utilizes Microsoft based technologies, it is not limited thereto.

The preferred embodiment of the healthcare information system illustrated herein presents information in the context of what users need to perform their jobs, such as by allowing users to drill down through forms to the level of detail required and take action. Graphic field descriptions, drop-down boxes, and icons may also be included to reduce the chance of errors and to simplify learning. The healthcare information system also preferably includes embedded analytics that empower users to proactively automate, measure, and track business processes and results, to effortlessly share knowledge about costs, revenue and quality of care, and to actually track and measure itself, to support the measurement of benefits and return on investment.

From the moment a patient enters the healthcare system—at any point—the present embodiment quickly and accurately captures complete clinical and financial information for access throughout the enterprise, eliminating guesswork and redundancy. The present embodiment can also help improve delivery of care by organizing all clinical activities around the patient. Workflow capabilities allow for timely clinical decisions, which can improve patient care. From a single screen, authorized clinicians can check a patient's medical history including medical images, place orders, track the status of patient care, and determine the appropriate next steps.

Figure 2:
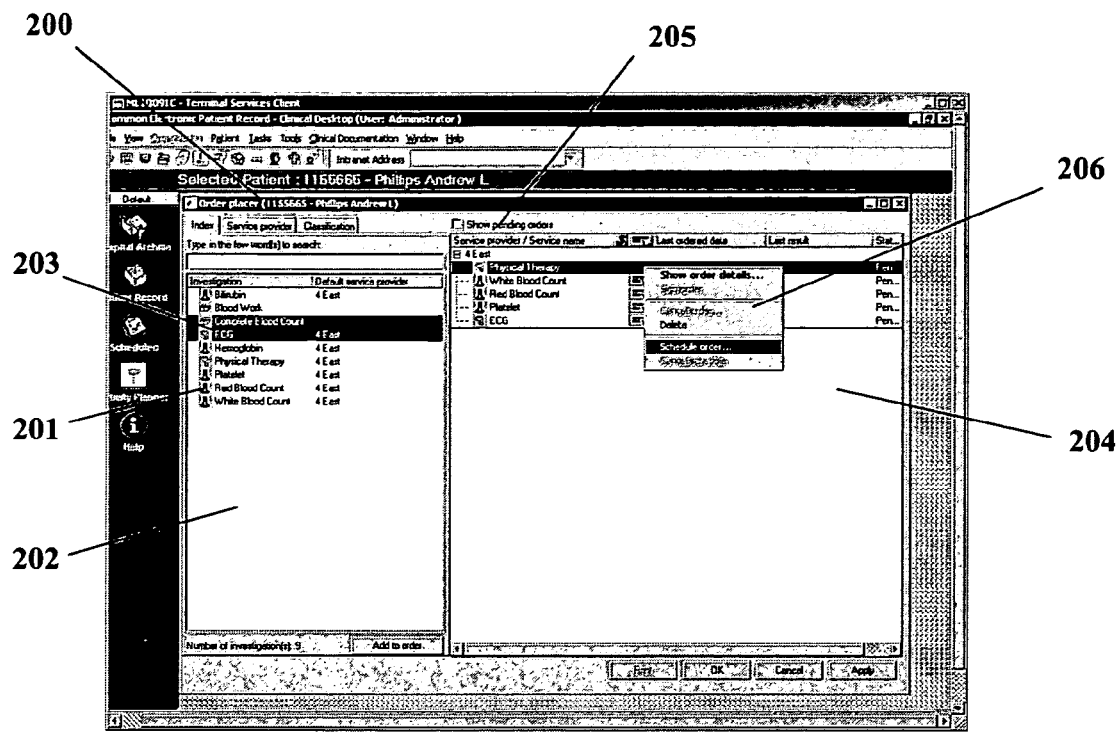
FIG. 2 is a computer screen shot of a preferred embodiment of an order entry display screen in accordance with aspects of the invention.

FIG. 2 illustrates a preferred embodiment of a user interface for the order-placing portion of a healthcare system. The order placer provides functionality for the generation of an order for a medical service (or service request) based upon service order information. The placement of an order is preferably supported by a service catalog. The user selects services or packages (service sets) from the assortment contained in the service catalog as part of the service order information. The selected services or packages are used to generate a request.

The order placing input screen display image (200) is preferably used as a tool to create a service request and generate one or more orders for each service provider involved in the service request as part of the service order information. Preferably, but not necessarily, one service provider is included in a service request. A request may be created that groups orders from several providers together. In this case, the system preferably generates an order for each service provider.

The view of the display screen preferably includes service catalog (201). Service catalog (201) exposes the services that may be selected for the order. The left side of the screen is a service catalog browser (202), which is used to select a service (203) and place the order. A "look in" drop down selection menu is preferably incorporated in this browser that includes the following information: all of the services, unit favorites (which is the default value), and user definable favorites. Different tabs may be presented depending on the selection made by the user. When a service or a package is selected on the left side, the system will retrieve information about the content of this order from data source 102, and then present it on the right side of the display screen (204), preferably as one row for each single order or test for the requested service A "show order list" check box (205) is preferably used to show the current generated orders for the patient, as predefined by the user and/or the healthcare organization. By default (when the display screen is first presented), the generated order list is preferably not shown, unless predefined to show in a set of user and/or organization configuration settings. Current orders on the order list are preferably visually differentiated from new orders in an order session summary. New orders are preferably indicated by a visually distinctive convention, such as "NEW" in front of each order in the user's order session summary in a different front than the existing orders in the order list, and are grouped together at the bottom of the right side of the display screen (204). The user may then preferably select to generate an order by double clicking on the service (investigation) or through a popup menu.

When an order is placed (generated) for a service that is schedulable, the system preferably checks the user's security access rights to the system to determine whether the user is authorized to schedule appointments. If the user is authorized to schedule appointments, a menu option to schedule the order is enabled (206). Selection of the "Schedule Order" option on the user interface causes the system to launch a "Find Appointment" form, which is presented on the user interface display screen, appropriately loaded with the service information from the order from data source 102. Alternatively, this form may launch automatically when the order is placed, without need to separately select the schedule option.

Figure 3:
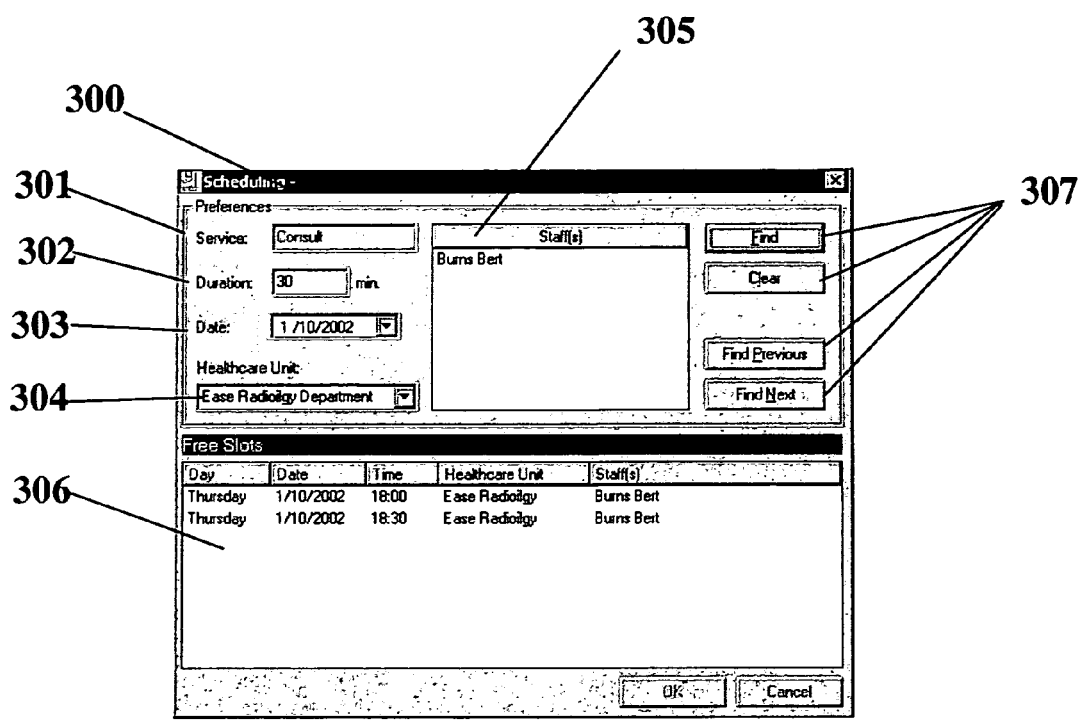
FIG. 3 is a computer screen shot of a preferred embodiment of an appointment finding form display screen in accordance with aspects of the invention.

An example of a preferred embodiment of a "Find Appointment" form is shown in FIG. 3. As shown in FIG. 3, the find appointment form 300 may include all of the service information from the order, such as the type of service (301), the duration (302), the preferred date for scheduling the appointment (303), the health care unit (304), the staff involved (305), and any free time slots that are available for performing the service (306). The user may run through the services sequentially, or may search them using the navigating buttons (307).

The user may optionally select a preferred provider if more than one provider is defined to deliver the service. The user can also modify the search date range parameters. When the user initiates a search, the system searches the information in data source 102 to determine available appointment times. This information is then presented to the user on the user interface display screen as a list of available appointment times. The user selects one of the available times and instructs the system to book that appointment. When the appointment is scheduled by the user using this form, the associated order's status is updated from 'Pending' to 'Scheduled' in data source 102.

If the appointment search finds that no appointments are available for the desired date range, three options are preferably presented to the user. The first is an option to add the request with its associated parameters to a waitlist, which is stored in data source 102. The second is an option to book the first available appointment, in addition to adding the request with its associated parameters to the waitlist. The third is to "ignore" or "cancel" the appointment request.

When the first option is chosen, no appointment is booked and the original request is transferred to the queued work list of waitlisted appointments stored in data source 102. The waitlist preferably contains information about the order, such as the tests included in the order, patient information (e.g., name and patient identifier), the provider or providers, the desired dates and times to schedule the appointment with order of preference, and the like.

Figure 4:
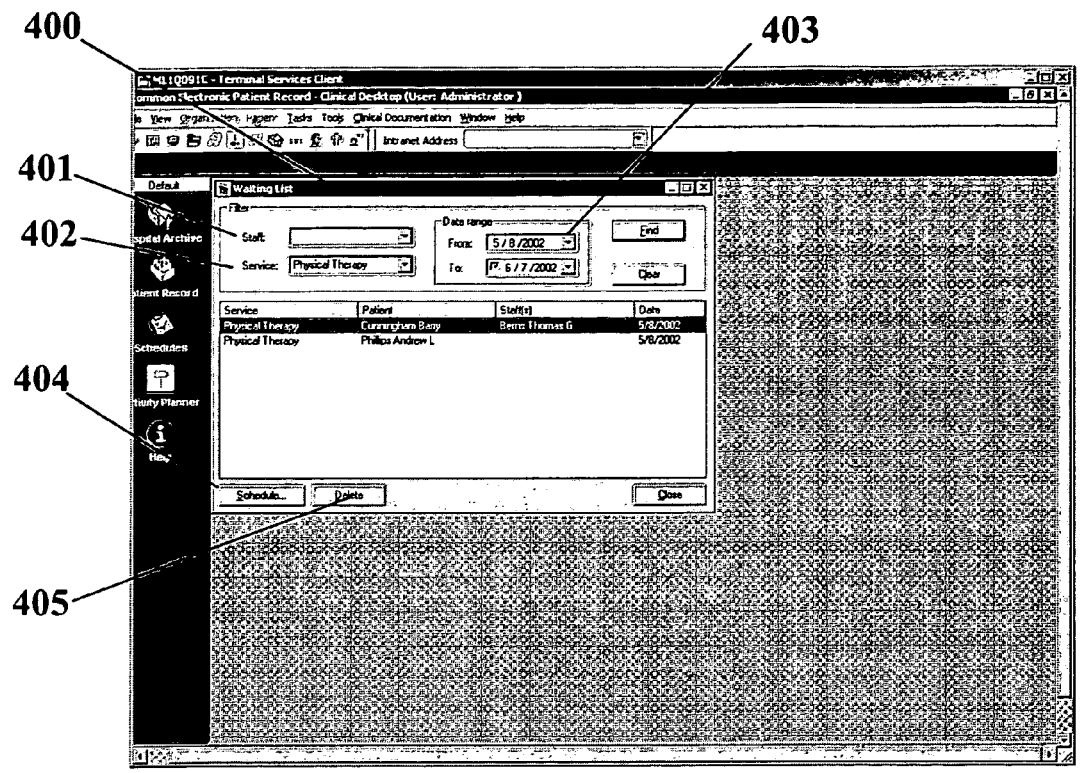
FIG. 4 is a computer screen shot of a preferred embodiment of a waitlist display screen in accordance with aspects of the invention.

FIG. 4 exemplifies a preferred embodiment of a user interface for the waitlist portion of a healthcare system. As shown in FIG. 4, waiting list input form 400 allows the user to include certain information, such as the staff (401), the service (402), and the desired dates for an appointment (403). The wait list form also allows the user to schedule the appointment (404), or delete the appointment (405). This is discussed in more detail below.

The waitlist stored in data source 102 may also be accessed directly by authorized users. Further, it may be sorted based upon one or more pieces of information contained in the entry for that order on the waitlist, for example, chronologically, by desired service, or by desired provider. Entries preferably remain on the waitlist until they are manually rescheduled by the user or are moved automatically by the system to an aged waitlist (also stored in data source 102), for supervisory follow-up when the desired appointment date is equal to the current date and no appointment was booked according to the second option.

When the second option is chosen, the system performs another search to find the first available appointment, plus the original request is transferred to the queued waitlist. When the user decides to book the first available appointment plus waitlist the request, the system performs a search in data source 102 to find the first available appointment. That appointment is booked and stored in data source 102, and in addition, an entry is added to the waitlist. This course of action will ensure that the patient books an appointment for the desired service, even though it is later than preferred.

The third option allows the user to exit the workflow without creating an entry on the waitlist. When the cancel appointment function is invoked, the waitlist is preferably surveyed for entries for the service (order) being cancelled, or the provider associated with the service being cancelled. If an entry is found on the waitlist that matches the service, the "Waitlisted Appointments" form is preferably again launched, loaded with the record information from data source 102 that matches the service being cancelled. If an entry is found on the waitlist that matches the provider, and the duration of the appointment being cancelled is greater than or equal to the duration required for the service on the waitlist, the "Waitlisted Appointments" form is preferably launched loaded with the record information from data source 102 that matches the provider for the service being cancelled.

Figure 5:
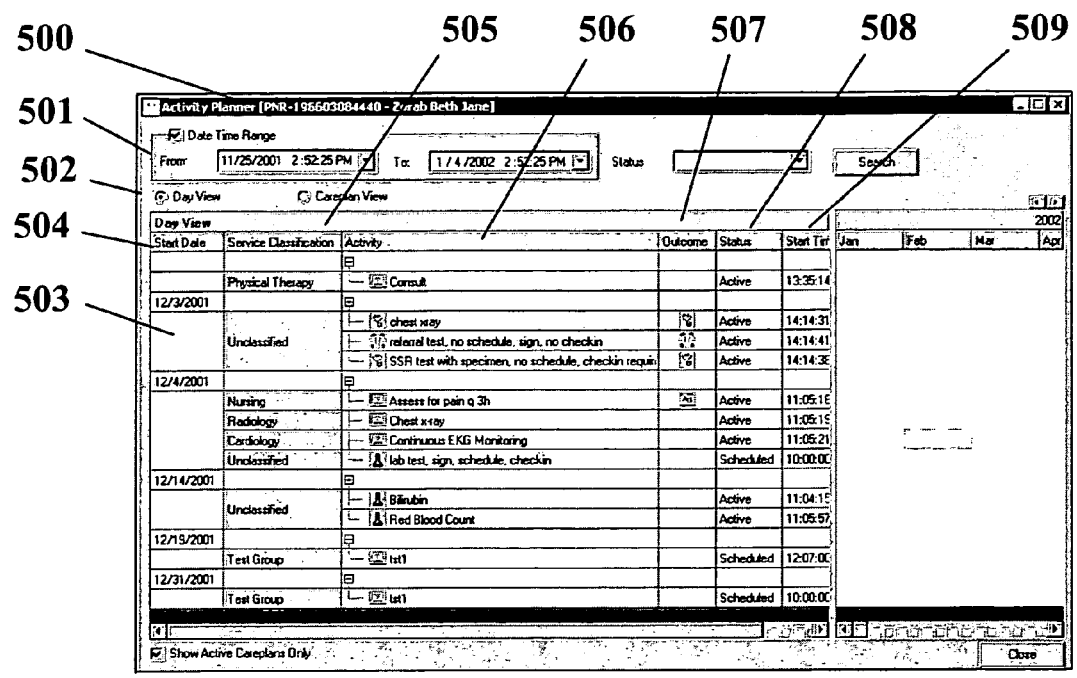
FIG. 5 is a computer screen shot of a preferred embodiment of an activity planner display screen in accordance with aspects of the invention.

FIG. 5 is a computer screen shot of an activity planner in accordance with aspects of the invention that shows the user the appointments that are scheduled during a given period of time or based upon a given care plan. As shown in FIG. 5, activity planner 500 may include a user selectable date range (501), a selection between a daily view and a view based upon care plans (502), and a window for viewing the activity information (503). In the day view mode, this information window preferably includes the start date for each activity (504), its service classification (505), a breakdown of the activities for the service (506), the outcome for the service (507), its status (508), and the scheduled start time for the appointment (509).

Figure 6:
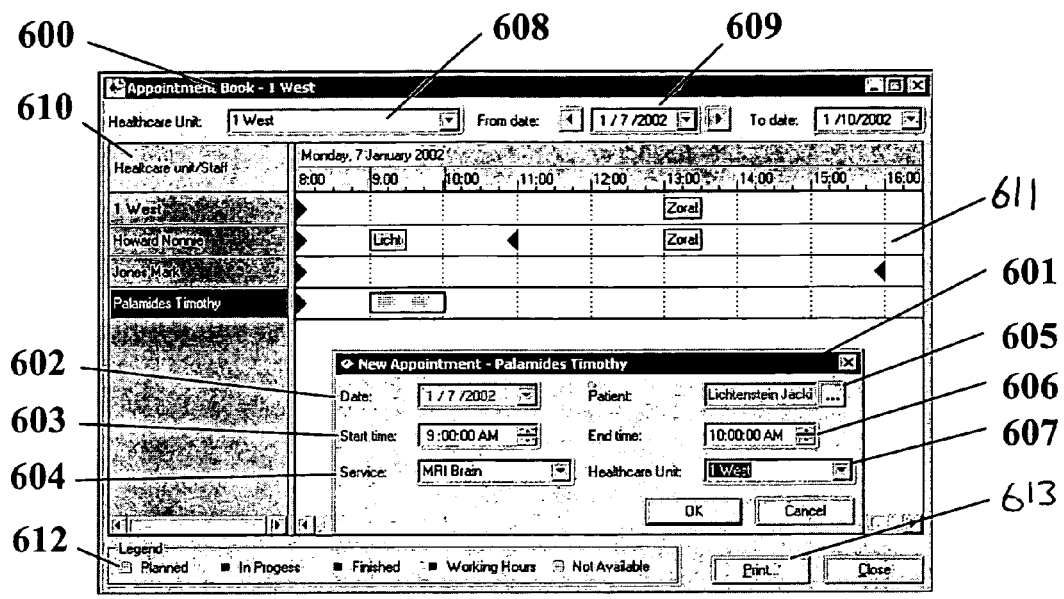
FIG. 6 is a computer screen shot of preferred embodiment of an appointment book display screen in accordance with aspects of the invention.

FIG. 6 is a computer screen shot illustrating the scheduling of an appointment and the appointment book in accordance to the aspects of the invention. As shown in FIG. 6, appointment book 600 includes a new appointment form (601) by which patients may input the information for scheduling the appointment. This information may include, for example, the date of the appointment (602), the start time (603), the service (604), the patient for whom the service is being performed (605), the end time of the appointment (606), and the health care unit (607). The appointment book also allows the user to view appointments scheduled for a given day, for example. These may preferably be filtered using a dropdown box for the particular health care unit (608), or a particular date range (609). The health care unit/staff may then be listed on the left side of the display screen (610), with the appointment information shown chronologically on the right side of the screen (611). A legend (612) may also be included, which shows the designations used for the appointment (e.g., planned, in progress, finished, working hours, and not available). The appointment information may also be printed (613).

Figure 7:
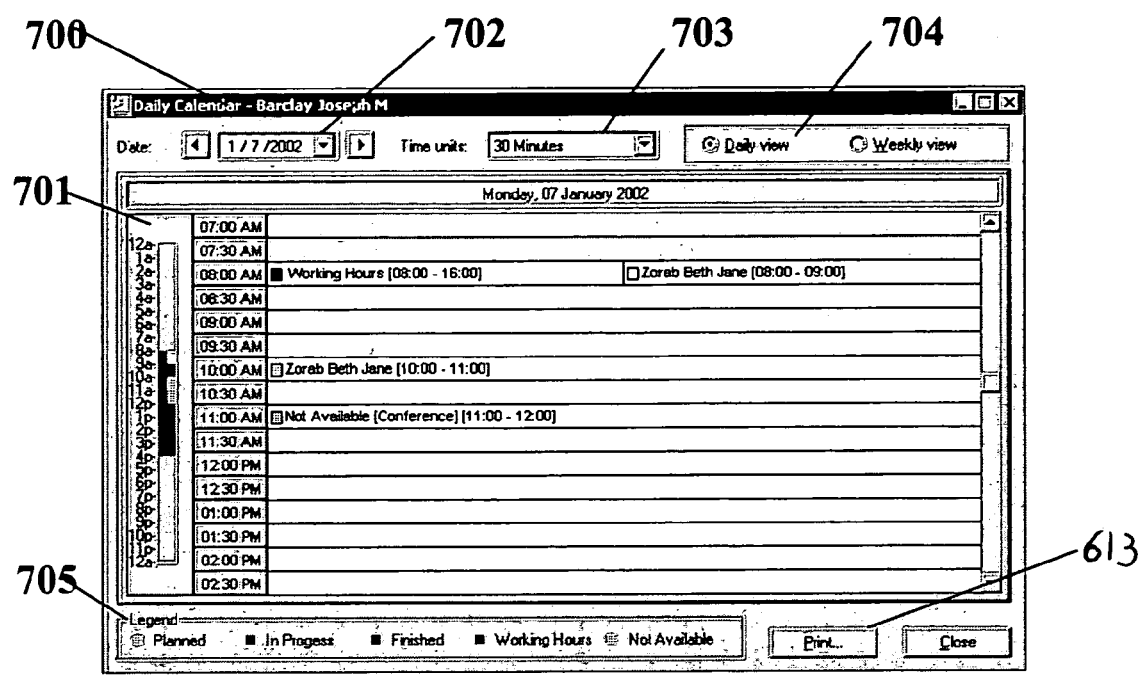
FIG. 7 is a computer screen shot of a preferred embodiment of a daily calendar display screen in accordance with aspects of the invention.

Users may also review appointment information in a daily calendar, shown in FIG. 7. Daily calendar 700 may include, for example, a window (701) showing time slots for a given day and various appointments that are scheduled for those times. As with the appointment book, the user may select the date shown (702). The user may also select the time intervals (703), and select between a daily and weekly view (704). The daily calendar may also include the legend (705), and allow for a printing of the calendar (613).

Figure 8:
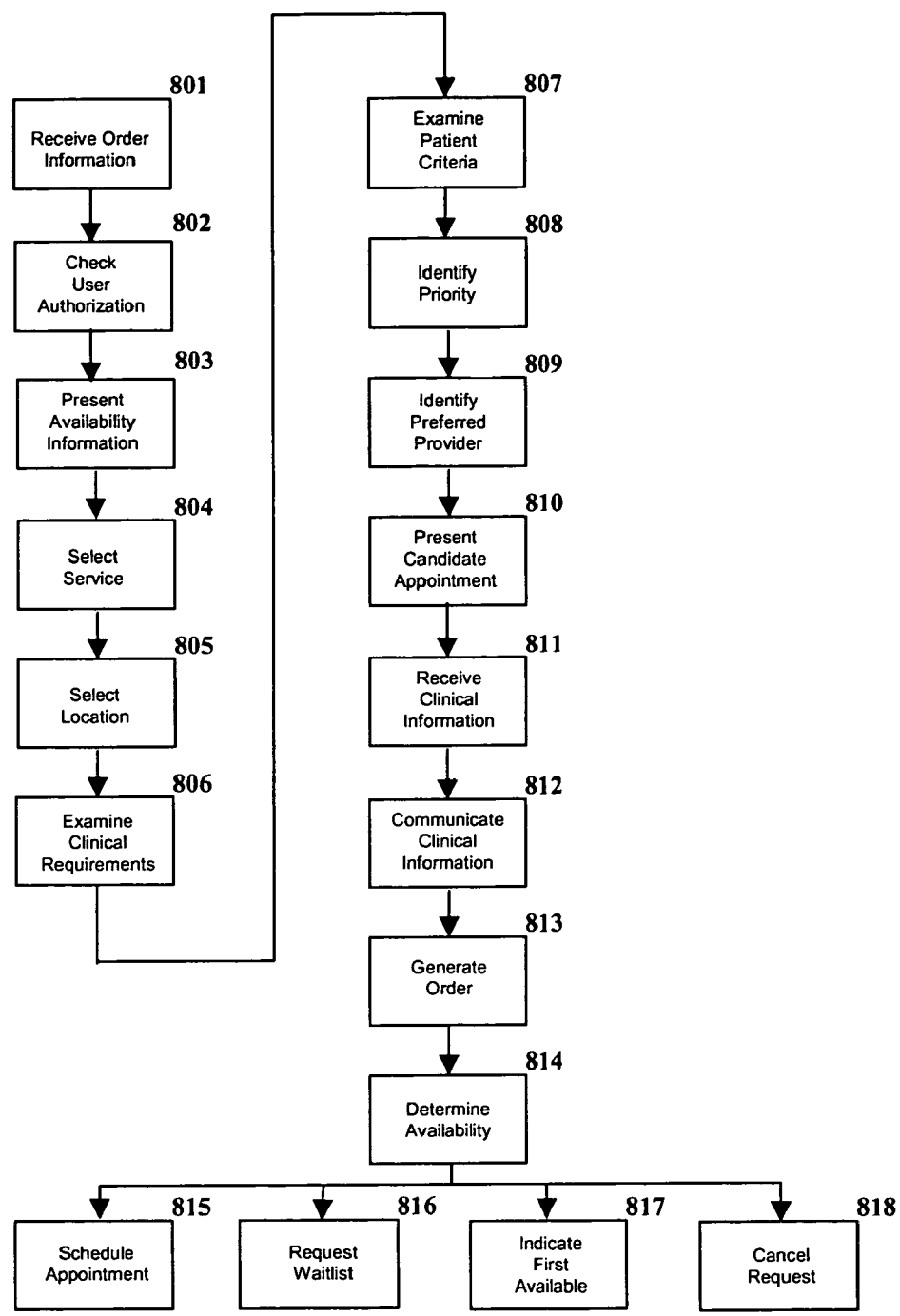
FIG. 8 is a flow chart illustrating the preferred functionality of the invention.

FIG. 8 is a flowchart illustrating the functionality of the preferred embodiment of the system of the invention. First, the system receives a message signaling generation of an order for a patient to receive said medical service (801). The system then preferably requests user identification information from the user and determines whether the user is authorized to schedule an appointment for the medical service (802). The user should be authorized to perform one or more tasks selected from the group consisting of (a) scheduling an appointment with a provider of said medical service, (b) storing said order information in a queued waitlist, and (c) automatically rescheduling said appointment based upon said queued waitlist.

Once the user has been authorized, the system presents appointment availability information (803) from data source 102 to the user through user interface 103, 104 in an appointment finder display image. The system then enables the user to schedule an appointment with a provider of the medical service for the patient to receive the medical service, as further described below. The user is preferably automatically prompted to schedule the appointment either at the time the order information is received or as determined by the waitlist queue. Alternatively, the appointment availability information may be presented to the user in response to the user's own initiating of the scheduling of an appointment through user interface 103, 104.

The appointment availability information preferably includes data for presentation to the user in an appointment finder display image for scheduling an appointment for at least one of a plurality of different medical services (804). The medical service may include, for example, one or more selected from the group consisting of (a) radiology, (b) MRI (Magnetic Resonance Imaging), (c) laboratory sample acquisition and testing, (d) surgery, (e) X-ray, (f) physical therapy, and (g) a medication administration. The medical services may also be administered to the patient at a plurality of different locations associated with one or more buildings, which information is also presented to the user for selection (805).

The system may then examine the clinical requirements for receiving the medical service (806) and patient criteria (807) to determine a candidate appointment to accomplish at least one of (a) avoiding a conflict with clinical requirements of another scheduled appointment, and (b) scheduling an appointment compatible with clinical requirements of another appointment. The system may also derive the candidate appointment by considering at least one of (a) a physical location for administering said medical service, and (b) a scheduled time and date of a prior or subsequent appointment. The system may also enable the user to schedule the appointment after identifying for the user the priority of the order in relation to other orders (808), and/or a preferred provider of the medical service (809). This information is presented to the user (810).

The system may also receive clinical information for the patient (811) for use by the provider in providing the medical service, and communicate the received clinical information to the provider (812) to enable the provider to use the clinical information in providing the medical service. The system may then generate the order for the patient to receive the medical service (813).

The system preferably determines whether a desired appointment with the provider of the medical service is available (814), and in response to this determination schedules the appointment (815) or performs at least one of (a) adding a request for said desired appointment to a waitlist (816), (b) indicating a first available appointment is to be scheduled for said patient (817), or (c) canceling a search request for an appointment (818), depending upon the user command.

The system may also update an appointment schedule for the provider of the medical service to indicate the scheduled appointment, may reschedule an appointment (either automatically or in response to user command), and may schedule an appointment for orders as they are drawn from the waitlist queue, as previously described.

It will be understood by those of ordinary skill in the art that while the functionality described above need not be performed in the order presented herein and portions need not necessarily be performed to achieve the claimed invention.

The present embodiment thus provides significant benefits over the systems of the prior art. Patient care is improved through earlier delivery of schedulable services. Customer satisfaction is improved through more convenient and/or earlier available appointment times and through ability to schedule multiple appointments on the same date. This embodiment also provides greater user productivity by eliminating the costly division of labor between the ordering and the scheduling processes. It provides improved management of scarce resources, improved customer satisfaction through earlier, more convenient appointment times, and improved resource utilization. This embodiment also provides improved resource utilization by rebooking timeslots that are freed up when an existing appointment is cancelled. These timeslots are often available on short notice, so having a list of patients, who are eager for an appointment, even if it is on short notice, improves the rebooking rate.

Although this invention has been described with reference to particular embodiments, it will be appreciated that many variations may be resorted to without departing from the spirit and scope of this invention as set forth in the appended claims. For example, the embodiments disclosed herein incorporate a single application server; while one of ordinary skill in the art will appreciate that any number of computer system application servers, data servers, and Web servers may achieve the same results. Similarly, the software of the present invention can comprise a single application having individual components or a suite of applications, and its form is not particularly limited.

What is claimed is:

1. A system for use in healthcare administration for integrating entry of an order for a medical service for a patient with the scheduling of a patient appointment for performing said medical service comprising:
   a user interface providing at least one display image enabling a user to enter service order information for a medical service to be provided to a patient;
   an interface for receiving data representing service order information for said medical service to be provided to said patient; and
   an integrated order placement and appointment scheduling system for generating data representing an order for said medical service to be provided to said patient in response to said receiving said service order information and in response to said generating data representing an order, automatically initiating generation of data representing a display image element enabling a user to schedule an appointment for said medical service to be provided to said patient using service order information.

2. A system according to claim 1, wherein
   said integrated order placement and appointment scheduling system automatically determines whether said user is authorized to schedule an appointment for said medical service using said user information and inhibits said user from scheduling an appointment if said user is unauthorized and automatically prompts said user to schedule said appointment.

3. A system according to claim 1, wherein said integrated order cement and appointment scheduling system presents appointment availability information to said user in response to said user initiating scheduling of an appointment.

4. A system according to claim 3, wherein said appointment availability information comprises data for presentation to said user in an appointment finder display image for scheduling an appointment for at least one of a plurality of different medical services.

5. A system according to claim 4, wherein said plurality of different medical services are administered to said patient at a plurality of different locations associated with one or more buildings.

6. A system according to claim 1, wherein
said display image element enabling a user to schedule an appointment for said medical service enables a user to launch a display image window to find an appointment and is populated with service order information and
said medical service includes one or more selected from the group consisting of (a) radiology, (b) MRI (Magnetic Resonance Imaging), (c) laboratory sample acquisition and testing, (d) surgery, (e) X-ray, (f) physical therapy, and (g) a medication administration.

7. A system according to claim 1, wherein said integrated order placement and appointment scheduling system presents a candidate appointment to said user derived by examining clinical requirements for receiving said medical service indicated in said service order information in order to accomplish at least one of (a) avoiding a conflict with clinical requirements of another scheduled appointment, and (b) scheduling an appointment compatible with clinical requirements of another appointment.

8. A system according to claim 1, wherein said integrated order placement and appointment scheduling system presents a candidate appointment to said user derived by considering at least one of (a) a physical location for administering said medical service, and (b) a scheduled time and date of a prior or subsequent appointment.

9. A system according to claim 1, wherein said integrated order placement and appointment scheduling system presents enables said user to schedule said appointment after identifying for said user a priority of said order in relation to other orders.

10. A method system according to claim 1, wherein said integrated order placement and appointment scheduling system presents enables said user to schedule said appointment after identifying for said user a preferred provider of said medical service.

11. A method system according to claim 1, further
wherein said integrated order placement and appointment scheduling system,
receives clinical information for said patient for use by said provider in providing said medical service, and
communicates said received clinical information to enable said provider to use said clinical information in providing said medical service.

12. A method system according to claim 1, wherein said display image element comprises a display image window enabling a user to find an appointment and is populated with service order information.

13. A system according to claim 1, wherein said integrated order placement and appointment scheduling system updates an appointment schedule for said provider of said medical service to indicate said scheduled appointment.

14. A system according to claim 1, wherein said integrated order placement and appointment scheduling system determines whether a desired appointment with said provider of said medical service is available and in response to said determination, performs at least one of, (a) adding a request for said desired appointment to a waitlist, (b) indicating a first available appointment is to be scheduled for said patient and (c) canceling a search request for an appointment.

15. A system according to claim 1, wherein said integrated order placement and appointment scheduling system,
receives user identification information from said user; and
determines whether said user is authorized to schedule an appointment for said medical service using said user information;
wherein said system determines said user is authorized to perform one or more tasks selected from the group consisting of (a) scheduling an appointment with a provider of said medical service, (b) storing said order information in a queued waitlist, and (c) automatically rescheduling said appointment based upon said queued waitlist.

16. A method for scheduling a patient appointment for receiving a medical service comprising the steps of:
enabling user entry of data representing an order for a patient to receive said medical service via a user interface;
using an integrated order placement and appointment scheduling system for generating data representing an order for said medical service to be provided to said patient in response to said entry of data and in response to generation of data representing an order, automatically initiating generation of data representing an appointment finder display image enabling a user to schedule an appointment for said medical service to be provided to said patient using service order information;
providing appointment availability information from a data source to said user interface in said appointment finder display image; and
enabling a user to use said user interface to schedule an appointment with a provider of said medical service for said patient to receive said medical service in response to said data representing an order.

17. A method according to claim 16, wherein said appointment availability information is provided in response to at least one of (a) user command, and (b) said entered data and said appointment finder display image enables a user to find an appointment and is automatically populated with service order information.

18. An apparatus for integrating entry of an order for a medical service for a patient with the scheduling of an appointment for performing said medical service in a healthcare system, said apparatus comprising:
a user interface for submitting service order information for said medical service for said patient from a user; and
an integrated order placement and appointment scheduling system for generating data representing an order for said medical service to be provided to said patient in response to said submitting said service order information and in response to said generating data representing an order, automatically initiating generation of data representing a display image element enabling a user to schedule an appointment for said medical service to be provided to said patient using service order information, said integrated order placement and appointment scheduling system including, an interface processor programmed to generate an order for said medical service based upon said service order information; and to enable said user to perform one or more tasks selected from the group consisting of (a) scheduling an appointment with a provider of said medical service, (b) storing said order information in a queued waitlist, and (c) automatically rescheduling said appointment based upon said queued waitlist using said user interface; and a data source programmed for storing one or more of (i) said service order information, (ii) said order, (iii) said scheduled appointment, (iv) said queued waitlist and (v) said rescheduled appointment.

19. An apparatus according to claim 18, wherein said interface processor is further programmed to automatically prompt said user to schedule said appointment using a computer system.

20. An apparatus according to claim 18, wherein said data source is further programmed to store appointment availability information, and wherein said interface processor is further programmed to present said appointment availability information to said user in response to said user initiating scheduling of an appointment through said user interface.

21. An apparatus according to claim 20, wherein said appointment availability information comprises data for presentation to said user in an appointment finder display image on said user interface for scheduling an appointment for at least one of a plurality of different medical services.

22. An apparatus according to claim 21, wherein said plurality of different medical services are administered to said patient at a plurality of different locations associated with one or more buildings.

23. An apparatus according to claim 18, wherein said medical service includes one or more selected from the group consisting of (a) radiology, (b) MRI (Magnetic Resonance imaging), (c) laboratory sample acquisition and testing, (d) surgery, (e) X-ray, (f) physical therapy, and (g) a medication administration.

24. An apparatus according to claim 18, wherein said interface processor is further programmed to present a candidate appointment to said user on said user interface derived by examining clinical requirements for receiving said medical service in order to accomplish at least one of (a) avoiding a conflict with clinical requirements of another scheduled appointment, and (b) scheduling an appointment compatible with clinical requirements of another appointment.

25. An apparatus according to claim 18, wherein said interface processor is further programmed to present a candidate appointment to said user derived by considering at least one of (a) a physical location for administering said medical service, and (b) a scheduled time and date of a prior or subsequent appointment.

26. An apparatus according to claim 18, wherein said interface processor is further programmed to enable said user to schedule said appointment after identifying for said user a priority of said order in relation to other orders using said user interface.

27. An apparatus according to claim 18, wherein said interface processor is further programmed to enable said user to schedule said appointment after identifying for said user a preferred provider of said medical service.

28. An apparatus according to claim 18, wherein said interface processor is further programmed to receive clinical information for said patient for use by said provider in providing said medical service, and communicating said received clinical information to enable said provider to use said clinical information in providing said medical service.

29. An apparatus according to claim 18, wherein said interface processor is further programmed to generate an order for a patient to receive said medical service.

30. An apparatus according to claim 18, wherein said interface processor is further programmed to update an appointment schedule for said provider of said medical service to indicate said scheduled appointment.

31. An apparatus according to claim 18, wherein said interface processor is further programmed to determine whether a desired appointment with said provider of said medical service is available and in response to said determination, programmed to perform at least one of (a) adding a request for said desired appointment to a waitlist, (b) indicating a first available appointment is to be scheduled for said patient, and (c) canceling a search request for an appointment.

32. An apparatus according to claim 18, wherein said integrated order placement and appointment scheduling system,
receives user identification information from said user; and
determines whether said user is authorized to schedule an appointment for said medical service using said user information;
wherein said system determines whether said user is authorized to perform one or more tasks selected from the group consisting of (a) scheduling an appointment with a provider of said medical service, (b) storing said order information in a queued waitlist, and (c) automatically rescheduling said appointment based upon said queued waitlist.

* * * * *